US010117432B2

(12) United States Patent
McIver et al.

(10) Patent No.: US 10,117,432 B2
(45) Date of Patent: Nov. 6, 2018

(54) ISOFLAVONOID COMPOUNDS AND USE THEREOF

(75) Inventors: John McIver, Dundas (CA); Chunquan Chen, Cambridge (CA); Birgit Schultz, Ste-Anne-de-Bellevue (CA); Hannah McIver, Oakville (CA)

(73) Assignee: Novozymes BioAg A/S, Bagsvaerd (DK)

( * ) Notice: Subject to any disclaimer, the term of this patent is extended or adjusted under 35 U.S.C. 154(b) by 2317 days.

(21) Appl. No.: 11/919,886

(22) PCT Filed: Mar. 18, 2005

(86) PCT No.: PCT/CA2005/000424
§ 371 (c)(1),
(2), (4) Date: Jan. 26, 2009

(87) PCT Pub. No.: WO2005/087005
PCT Pub. Date: Sep. 22, 2005

(65) Prior Publication Data
US 2009/0305895 A1  Dec. 10, 2009

(30) Foreign Application Priority Data

Mar. 18, 2004  (CA) .................................... 2461261
Jun. 17, 2004   (CA) .................................... 2470669

(51) Int. Cl.
*A01N 43/16* (2006.01)
*A01N 63/04* (2006.01)
*A01N 43/32* (2006.01)

(52) U.S. Cl.
CPC .............. *A01N 43/16* (2013.01); *A01N 43/32* (2013.01); *A01N 63/04* (2013.01); *Y02A 40/143* (2018.01)

(58) Field of Classification Search
CPC combination set(s) only.
See application file for complete search history.

(56) References Cited

U.S. PATENT DOCUMENTS 5,141,745 A  8/1992  Rolfe
5,229,113 A  7/1993  Kosslak et al.

FOREIGN PATENT DOCUMENTS

| CA | 2243669 | 1/2000 |
| CA | 2285727 | 4/2001 |
| CA | 2439421 | 10/2001 |
| CA | 2179879 | 2/2004 |
| EP | 245931 | 11/1991 |
| WO | WO97-26363 | 7/1997 |
| WO | WO-00-04778 | 2/2000 |
| WO | WO-01-26465 | 4/2001 |

OTHER PUBLICATIONS

Kucey et al. (Populations of Rhizobium leguminosarum biovars phaseoli and viceae in fields after bean or pea in rotation with nonlegumes, Canadian Journal of Microbiology, 35, 1989, pp. 661-667).*
Pan et al. (Genistein and Daidzein Concentrations and contents in roots of three soybean Cultivars Grun under Three Root Zone Temperatures, J. Agronomy & Crop Science 180, 77-82 (1998)).*
Palle Pedersen, "Soybean Growth and Development", Iowa State University, May 2004, pp. 1-28.
Supplementary European Search Report, dated May 8, 2009.
Gough, Clare et al., Specific Flavonoids Stimulate Intercellular Colonization of Non-Legumes by Azorhizobium Caulinodans; Biology of Plant-Microbe Interactions, 1997; pp. 409-415; vol. I; International Society for Molecular Plant-Microbe Interactions, St. Paul, Minnesota USA.
Begum et al.; Specific Flavonoids Induced Nod Gene Expression and Pre-Activated Nod Genes of Rhizobium Leguminasorum Increased Pea (*Pisum sativum* I.) and Lentil (*Lens culinaris* L.) Nodulation in Controlled Growth Chamber Environments; Journal of Experimental Botany; 2001; pp. 1537-1543; vol. 52, No. 360; Society for Experimental Biology.
Hopper, Waheeta et al.; Enhanced Nodule Formation in Legumes by Rhizobia Treated With Nod Factor Inducers; 22 PP; SPIC Science Foundation, India.
Begum et al; Inoculation of Pea (*Pisum sativum* L.) by Rhizobium Leguminosarum BV. Viceae Preincubated With Naringenin and Hesperetin or Application of Naringenin and Hesperetin Directly Into Soil Increased Pea Nodulation Under Short Season Conditions; Plant and Soil; 2001; pp. 71-80; vol. 237; No. 1; Kluwer Academic Publishers, Netherlands.
Prithiviraj, B. et al.; A Host-Specific Bacteria-to-Plant Signal Molecule (Nod Factor) Enhances Germination and Early Growth of Diverse Crop Plants;Chemical Abstracts Service, Columbus, OH, USA.
Broughton et al,, Plant and Soil, 252:129-37 (2003).
European Search Report for Application No. 15174192,3 dated Sep. 9, 2015.
Göttfert, *Communication between Rhizobia and plants*, in Bacterial Signaling, pp. 57-73 (2009).
Hungria and Stacey, Soil Biol, Biochern, 29(5/6):819-30 (1997).
Jain and Nainawatee J. Plant Biochemistry & Biotechnology, 11:1-10 (2002).

(Continued)

*Primary Examiner* — Johann R Richter
*Assistant Examiner* — Danielle Sullivan
(74) *Attorney, Agent, or Firm* — RatnerPrestia

(57)  ABSTRACT

The use of a one or more Isoflavonoid compound Signals which may be with an agriculturally acceptable carrier, applied prior to planting, up to 365 days or more, either directly to the seed or transplant of a non-legume crop or a legume crop, or applied to the soil that will be planted either to a non-legume crop or a legume crop, for the purpose of increasing yield and/or improving seed germination and/or improving carrier seed emergence and/or improving modulation and/or increasing crop stand density and/or improving plant vigour and/or improving plant growth, and/or increasing biomass, and/or earlier fruiting, all including in circumstances of seeding and plant transplanting.

27 Claims, 7 Drawing Sheets

(56) References Cited

OTHER PUBLICATIONS

Kamboj et al., Physiol. Mol. Biol. Plants, 16(1):69-77 (2010).
Peck et al., J. Bacteriol., 188(15):5417-27 (2006).
Recourt et al., J. Bacteriol., 171(8):4370-77 (1989).
Schlaman et al., J. Bacteriol., 171(9):4686-93 (1989).
Chinese Office Action dated Nov. 13, 2015 in Chinese Application No. 201310103257.5.
Chinese Search Report for Application No. 2013101032575 by Hui Cao dated Apr. 27, 2014 (with English Translation).
Webster et al., Plant Cell and Evironment, 21:373-83 (1998).

\* cited by examiner

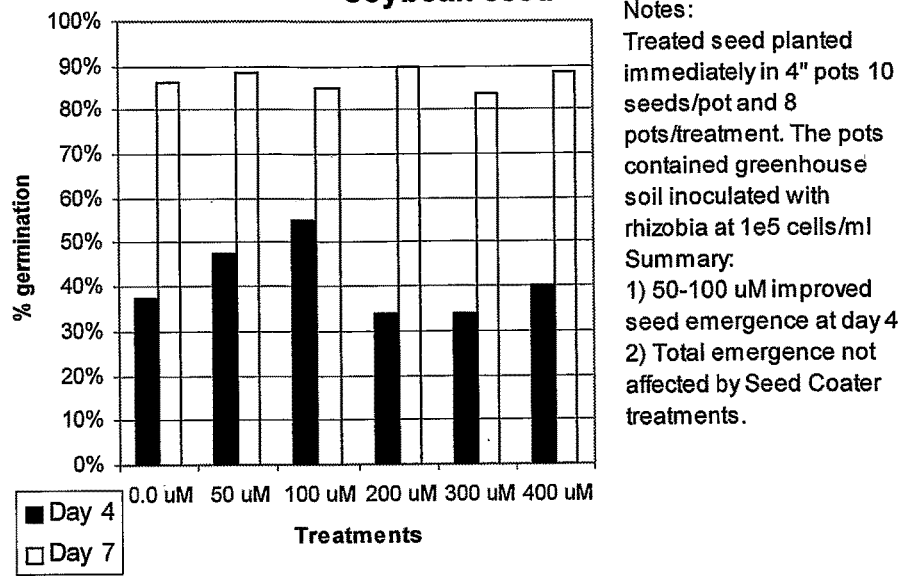

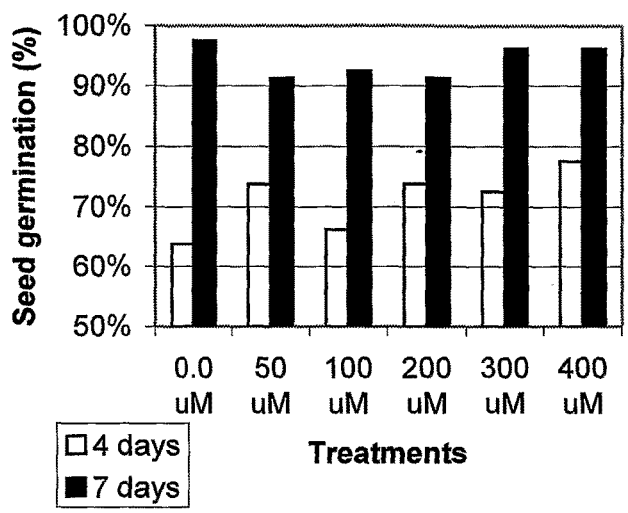

Fig 2. Soybean seed germination 1 month after treatment by seed coater

Notes:
One month after seed treatment, ten seeds were planted in 4" pots inoculated with rhizobia at 1e5 cells/ml, 8 pots/treatment.
Summary:
1) No negative effect was demonstrated by Seed Coater at any dose when stored for 1 month at room temperature.
2) Seed emergence was increased at day 4 by all treatments

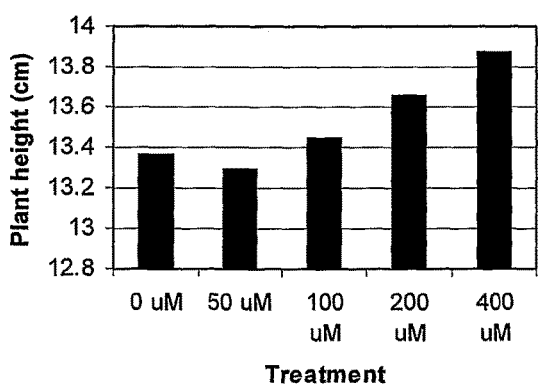

Fig 3. Effect of Seed Coat on soybean plant height

Notes; Treated seed planted immediately in 4" pots, 10 seeds/pot and 8 pot/treatment. Pots contained greenhouse soil inoculated with rhizobia at 1e5 cells/ml. Data were collected at day 24.
Summary; Treatments of Seed Coater from 100-400 uM improved plant height.

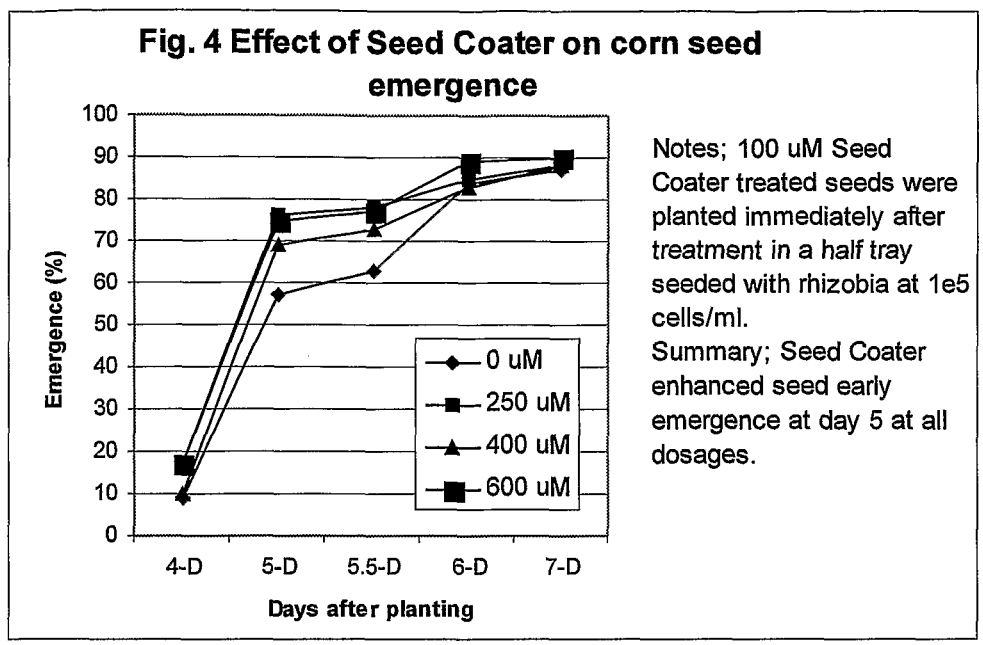

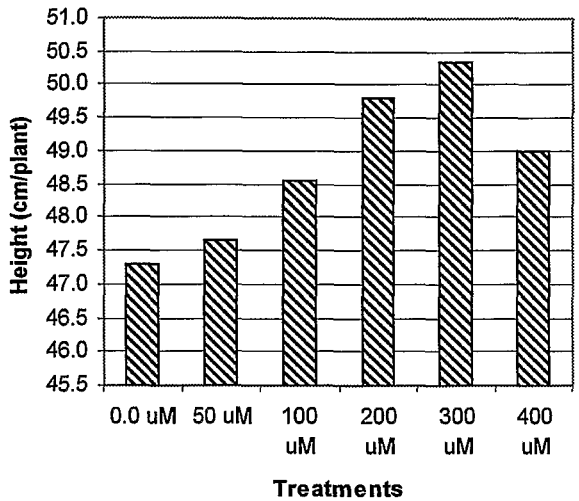

Fig. 5 Effect of Seed Coater on corn plant height

Notes; Seed Coater treated seed planted immediately in pots seeded with rhizobia at 1e5 cells/ml, 10 seeds/pot and 8 pots/treatment, and thinned to 2 plants/pot after emergence. Data were collected at day 27.

Summary; Increased plant height was demonstrated by all treatments with 300 uM showing the greatest height.

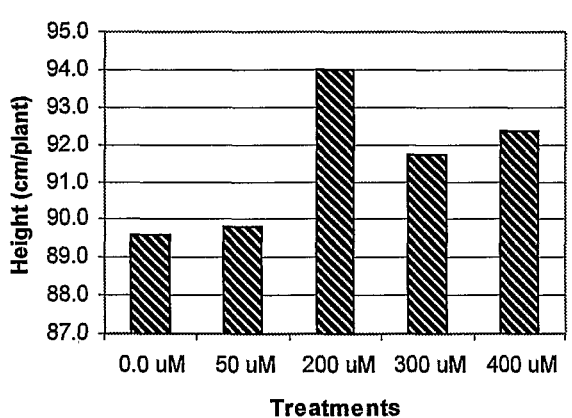

Fig. 6 Effect of Seed Coater on corn plant height

Notes; Seed Coater treated seeds were stored at room temperature for 1 month and planted in rhizobia seeded soil at 1e5 cell/ml in 5-inch pots, 10 seeds/pot, 8 pots/treatment, and thinned to 2 plants per pot after emergence. The data were collected at 32 days after sowing
Summary: Seed Coater at 200-400 uM increased plant height with 200 uM being the best treatment.

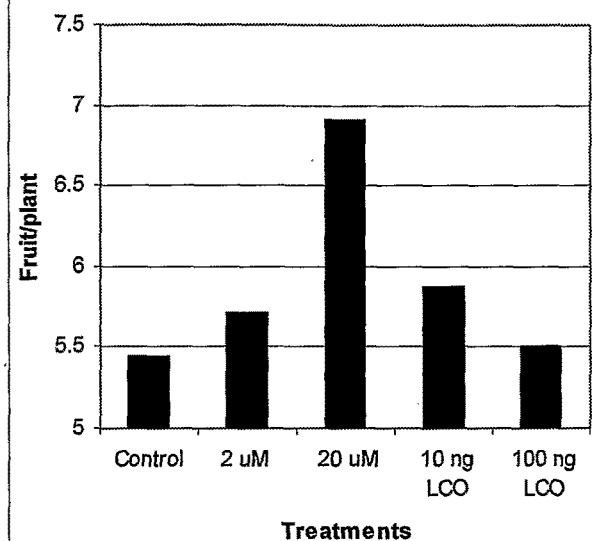
Fig. 7 Effect of SeedCoater transplant formulation on cherry tomato early fruit numbers

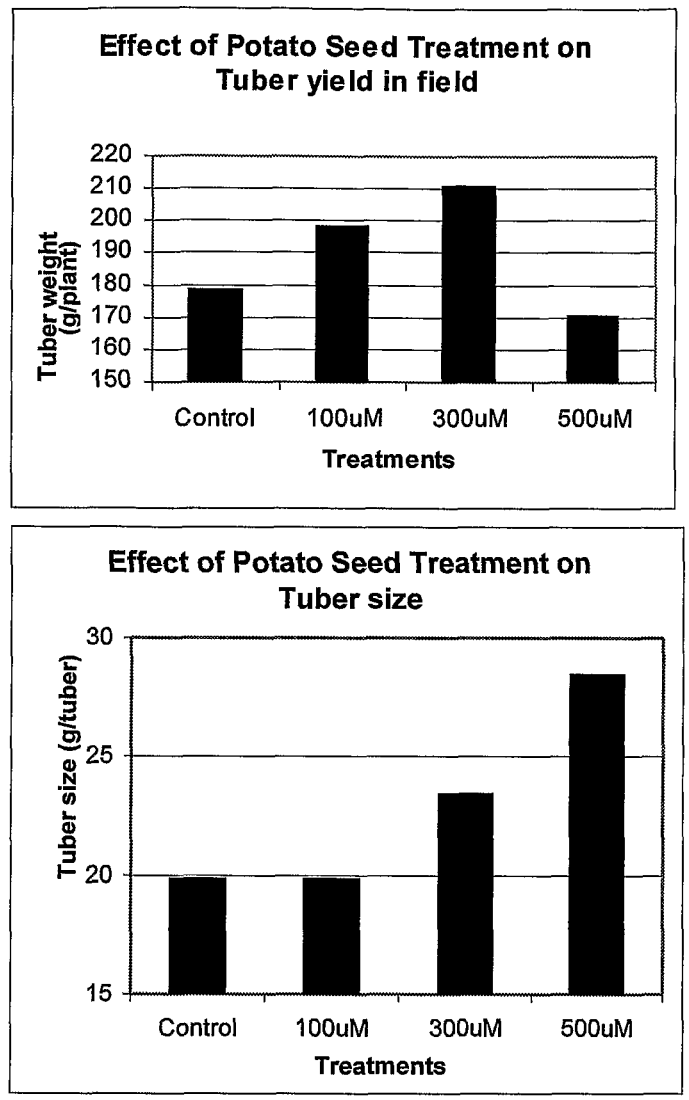
Figure 8. Growth promotion of potato tubers with signals grown in the field

Figure 9. Growth promotion of potato tubers with signals grown in the greenhouse, 2004
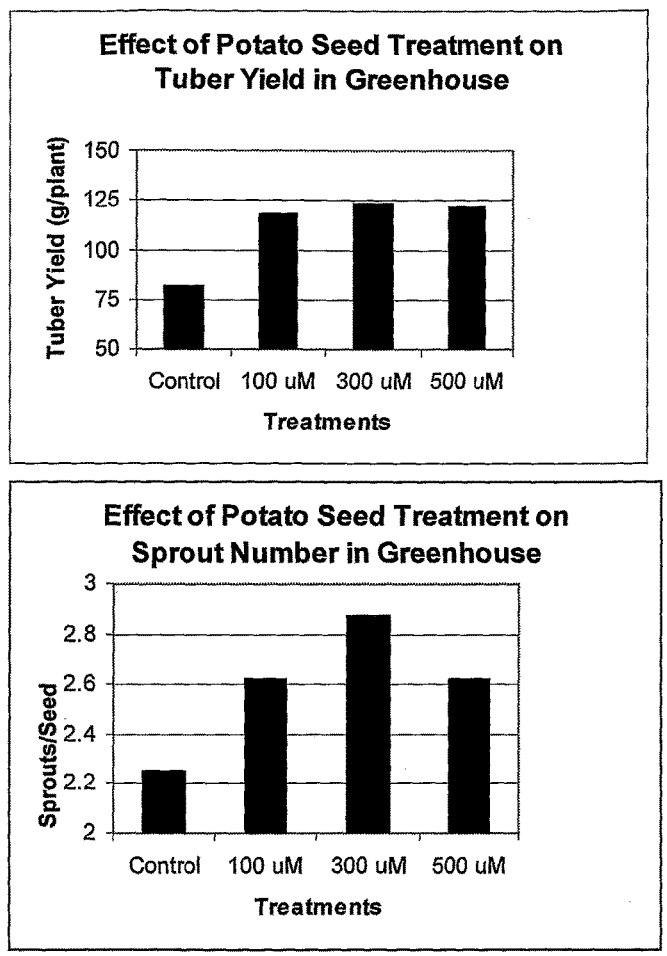

ISOFLAVONOID COMPOUNDS AND USE THEREOF

The invention relates to the use of a one or more Isoflavonoid compound Signals which may be with an agriculturally acceptable carrier, applied prior to planting, up to 365 days or more, either directly to the seed or transplant of a non-legume crop or a legume crop, or applied to the soil that will be planted either to a non-legume crop or a legume crop, for the purpose of increasing yield and/or improving seed germination and/or improving earlier seed emergence and/or improving nodulation and/or increasing crop stand density and/or improving plant vigour and/or improving plant growth, and/or increasing biomass, and/or earlier fruiting, all including in circumstances of seedling and plant transplanting.

BACKGROUND

Agricultural Practices

Agriculture in the developing world frequently utilizes a practice of intercropping plant species to maximize land productivity. That practice frequently involves a legume crop interspaced row by row with another plant species of regional value. It has long been known that the non-leguminous crop generally benefits in yield for having been in intimate contact at the root level with the legumes. This has traditionally been thought to be due to the legumes known benefit of returning fixed plant-utilizable nitrogen to the soil through the residual of its own nitrogen-fixing symbiosis with the rhizobia bacteria. This nitrogen, it was viewed, was utilized by the intercrop growing better.

In the developed world intercropping legumes with other agricultural crops, while known and understood, is simply not feasible. It is a practice requiring hand field maintenance for best results and in volume agriculture the equipment does not lend itself to the disparity in plant heights and size experienced i.e. soybeans (a legume) is physically much different from maize.

North American Cropping Practices

Intercropping practices from the developing world are, in developed countries, translated into crop rotation agricultural practices where a single crop is grown on the land one year and another crop is grown in the following year. These crops are so rotated as to best maintain the land and reduce its nutrient loss and may involve two, three or four crops in regular rotation year-by-year.

One of these crops will be a legume, the type depending on soil, markets, region etc and might involve soybeans, peas, beans, alfalfa, clover etc.—all legumes with their own symbiotic relationship with a particular rhizobia bacterial species—and each bacterial species producing a specific LCO structure for the particular plant species host.

It has long been held that the crop rotation must include a legume because of their ability to leave a nitrogen residue available to the following crop—that residue generally recognized to be a pound of Nitrogen for each bushel of legume seed harvested i.e. for soybeans 40-50 lbs N per acre available to the next, generally non-leguminous crop.

In North America the major crop rotations are (1) Corn-soybeans and used through the major production states of the USA—Illinois, Ohio, Iowa, Nebraska—and (2) Wheat-Peas, in western Canada.

Scientific Development

The legume symbiosis with rhizobia is now much better understood while not yet fully explained. It involves and requires a series of plant and microbial signals to initiate the plant tissue changes, which will protect and support the rhizobia internally to the root where it can undertake nitrogen gas conversion to plant utilizable nitrogen utilizing energy from the plant. Scientific and patent literature available to the skilled person, summarizing current knowledge include International Publication Number WO 00/04778, published Feb. 3, 2000 and WO 01/26465, published Apr. 19, 2001, both of Smith et al, and Canadian Serial Number 2,439,421, all incorporated herein by reference.

It is now known scientifically that the rhizobial signal sent to the legume plant to initiate root tissue changes is a Lipo-chito-oligosaccharide (LCO) and is termed Nod Factor in this application. Its production arises from the adjacent rhizobia bacteria receiving legume root exuded isoflavonoid chemicals—also termed Signals—that switch on the genes for the production of these LCOs. Signals are phenolic compounds, flavoned, isoflavones and flavanones, secreted by legume roots, which act as chemo-attractants to rhizobia and activators of the Nod genes.

It is further appreciated here through present studies and patents that LCOs have a plant growth function not restricted to legumes. It has been demonstrated that non-legume seeds as well as legume seeds germinate earlier in the presence of minute ($10^{-7}$ to $10^{-12}$ M) levels of LCO in solution.

It has been further demonstrated that foliar LCO applications to many plants (corn, soybeans, peas, tomatoes) leads to their earlier flowering and higher yield. The mechanism for these phenomena continues to be under study.

The relationship and interaction of Nod Factors, Signals, with LCOs produced by rhizobia has been the subject of considerable investigation. For examples in U.S. Pat. No. 5,141,745 Nodulation Inducing Factors, a principal object of this invention to identify a structurally related class of molecules, substituted flavones, which stimulate nodulation gene expression and elicit faster initiation of nodulation in legumes. The work describes the isolation and identification of substituted flavones which are nodulation gene-inducing factors. The invention relates in general to the field of legume-Rhizobium symbiosis and in particular to the identification of flavonoid compounds which stimulate expression of rhizobia nodulation genes and elicit faster rates of legume nodulation by rhizobia. These compounds are useful in general for selective control of gene expression and in particular in improved legume inoculating compositions.

In U.S. Pat. No. 5,229,113, "*Bradyrhizobium Japonicum* Nodulation Inducing Factor", The work describes the identification of chemical compounds that induce expression of nodulation genes of *Bradyrhizobium japonicum*.

It is a principal object of this invention to identify molecules which stimulate nodulation gene expression in strains of *B. japonicum*.

In Canadian Patent Number 2,179,879, "Composition for Enhancing Grain Yield and Protein Yield of Legumes Grown Under Environmental Conditions that Inhibit or Delay Nodulation", this patent relates specifically to the use of the nod factors genestein or daidzein plus a strain of *B. japonicum* on legumes, specifically soybeans, grown under environmental conditions that inhibit or delay nodulation, specifically low root zone temperatures between 17° C. and 25° C. It does not teach the use of the nod factor alone or in any other medium. It does not teach the use of nod factor alone or with any carrier in legumes grown under normal conditions. It does not envision the use of nod factor alone or with a carrier for use in non-legume crops.

While the relationship of Signals to LCOs and their effects on plants have been described under certain conditions, the effect of Signals and their compositions alone on the growth of non-legumes and legumes requires to be assessed.

The objects of the present invention include application and use of one or more Signals and compositions thereof to a non-legume including a seed, resulting in increased yield and/or improved seed germination, and/or improved emergence, and/or increased stand density, and/or increased biomass, and/or improved plant vigour, and/or improved plant growth and/or earlier fruiting; including but not limited to:

where the non-legume includes but is not limited to a seed, tuber, transplant, or vegetative cutting;

where the non-legume is grown for use in agriculture, horticulture, silviculture, or gardening;

where the non-legume is sown into land that had previously been sown to a legume crop, or which has an indigenous population of rhizobia;

where the non-legume is sown into land that had not previously been sown to a legume crop.

where a Signal is applied to the non-legume crop up to 365 days or more in advance of planting;

where a Signal is applied with an agriculturally acceptable carrier such as, but not limited to, water, liquid sugar solutions, seed treatments, inoculants, additives, extenders, herbicides, fungicides, insecticides, fertilizers, growth promoters, or horticultural media;

where the soil to be planted with the non-legume crop has been pre-treated with a specific symbiotic rhizobia or has an indigenous population of rhizobia;

where the seed has been treated with a specific symbiotic rhizobium or rhizobia.

A further object of the present invention includes one or more Signal and compositions thereof, and their use, applied to the soil which will be planted with a non-legume crop, resulting in increased yield and/or improved seed germination, and/or improved emergence, and/or increased stand density, and/or increased biomass, and/or improved plant vigour, and/or improved plant growth; and/or earlier fruiting, including but not limited to:

where the non-legume is grown for use in agriculture, horticulture, silviculture, or gardening;

where the non-legume is sown into land that had previously been sown to a legume crop or has an indigenous population of rhizobia;

where the non-legume is sown into land that had not previously been sown to a legume crop;

where a Signal is applied with an agriculturally acceptable carrier such as, but not limited to, water, seed treatments, inoculants, herbicides, fungicides, insecticides, fertilizers, growth promoters, or horticultural media;

where the soil to be planted with the non-legume crop has been pre-treated with a specific symbiotic rhizobium or rhizobia or has an indigenous population of rhizobia;

where the seed has been treated with a specific symbiotic rhizobium or rhizobia;

A still further object of the present invention includes one or more Signal and compositions thereof, and their use, applied to a legume including a seed, resulting in increased yield and/or improved seed germination, and/or improved emergence, and/or increased stand density, and/or increased nodule numbers, and/or increased nodule weight, and/or increased biomass, and/or improved plant vigour, and/or improved plant growth; and/or earlier fruiting, including but not limited to:

where the legume includes but is not limited to a seed, tuber, transplant, or vegetative cutting;

where the legume is grown for use in agriculture, horticulture, silviculture, or gardening;

where the legume is sown into land that had previously been sown to a legume crop or has an indigenous population of rhizobia;

where the legume is sown into land that had not previously been sown to a legume crop;

where the Signal is applied to the legume crop up to 365 days or more in advance of planting;

where the Signal is applied with an agriculturally acceptable carrier such as, but not limited to, water, seed treatments, inoculants, herbicides, fungicides, insecticides, fertilizers, growth promoters, or horticultural media;

where the soil to be planted with the legume crop has been pre-treated with a specific symbiotic rhizobium or rhizobia or has an indigenous population of rhizobia;

where the seed has been treated with a specific symbiotic rhizobia.

A still further object of the present invention includes one or more Signal and compositions thereof, and their use, applied to the soil, which will be planted with a legume crop, resulting in increased yield and/or improved seed germination, and/or increased stand density, and/or earlier emergence, and/or improved plant vigour, and/or improved plant growth, including but not limited to:

where the legume is grown for use in agriculture, horticulture, silviculture, or gardening;

where the legume is sown into land that had previously been sown to a legume crop or has an indigenous population of rhizobia;

where the legume is sown into land that had not previously been sown to a legume crop;

where the Signal is applied with an agriculturally acceptable carrier such as, but not limited to, water, liquid sugar solutions, seed treatments, inoculants, additives, extenders, herbicides, fungicides, insecticides, fertilizers, growth promoter, or horticultural media;

where the soil to be planted with the legume crop has been pretreated with a specific symbiotic rhizobium or rhizobia or has an indigenous population of rhizobia;

where the seed has been treated with a specific symbiotic rhizobium or rhizobia;

Thus, the present invention is directed to one or more Signals and agricultural compositions thereof, and their use applied to legumes and non-legumes up to 365 days or more prior to planting in methods, either directly to a plant or crop or indirectly to the soil that will be planted, to increase yield, and/or improve germination, and/or improve emergence, and/or increase stand density, and or increase biomass, and/or improve plant vigour, and/or improve plant growth, and/or result in earlier fruiting, and/or increase nodule weight, and/or increase nodule number, all including in circumstances of seed planting, of seedling and plant transplanting, or emergence of sprouts from tubers and development of new plants from higher plant perinating structures.

Surprisingly, inventors have found that Signals and compositions thereof are useful as aforesaid in legume and non-legume plant families, and in methods relating to the improvements and increases, all as aforesaid, including in conditions which limit growth, as well as optimal conditions for growth. The compositions and methods of the present invention find utility in growth limiting conditions, including conditions associated with pH stress, water stress and below or above an optimum temperature range, for plant or crop growth, germination, emergence and the like.

In accordance with the present invention, an "agricultural composition" and an "agriculturally effective amount of a composition" refer to a quantity sufficient, of one or more Signals, to result in a statistically significant enhancement, improvement or increase versus a control, as aforesaid, without detriment to plant, soil or crop. By "emergence" is meant observable growth above the rooting medium surface. By "germination" is meant observable root growth development from the embryo and by "field growth" is meant growth under conditions in the field as opposed to growth under more controlled conditions, such as in a greenhouse.

Seedling Growth-stimulant

A Seed Application of Soybean Isoflavonoid Signals

In intercropping, the response of the non-legume crop may be explained as in fact due to the LCOs produced by the legume (bean) plants migrating to the roots of the non-legume and initiating a growth response in that crop. This is a reasonable assumption with present knowledge.

In view of knowledge of agriculture, of soybeans and soybean crop rotations with corn and of Peas in rotation with wheat, of legume isoflavonoid signals which induce increased nodulation through increased LCO production, by the rhizobial cells, of manufacture and application of soybean and pea rhizobial seed-inoculants and the persistence of the rhizobia in soil, the present inventors have considered the application of soybean and other isoflavonoid signal in agriculturally effective and useful amounts to corn seed and other legume and non-legume species, including crop and horticultural varieties, including for transplanting, to cause the inducement of LCO production by the indigenous rhizobial population in the soil and that this LCO might lead to increased growth at the seedling stage when the young plants are being established and the other desirable effects all as aforesaid.

This concept was then broadened to encompass horticultural crops where the seeding and potting mix could be seeded with a level of Bradyrhizobium (for Soybeans) or of other Rhizobium species provided they were capable of inducement by their appropriate isoflavonoid signals to produce meaningful levels of LCO at the seedling roots where it could act as a growth stimulant to non-leguminous bedding plants and horticultural crops.

This was tested.

(1) Corn Growth Stimulation

Potting soil was seeded (inoculated) with sufficient *Bradyrhizobium japonicum* from a commercial soybean inoculant to attain 100,000 active cells per gram of soil, a level mid point to recognized rotational corn bean land where the soil population will be between 10,000 and 1,000,000 active bacterial cells per gram of soil.

Corn seed coated with various levels of the isoflavonoid inducer, genistein, were planted in this soil in pots in the greenhouse in such a way that germination could be determined as well as height differences from the untreated control over the first month of growth. The levels tested were 0, 50, 100, 200, 300 and 400 uM genistein solution applied at the rate of 0.3 ml (300 ul) per 100 corn seeds, a normal application rate in agriculture.

Further batches of such treated seed were stored in a dry cool 22° C. room for a period of up to 6 months and representative samples withdrawn monthly for retesting for germination and growth, thus determining the capacity of the concept for pre-treatment of seed from the previous harvest at harvest time. These studies continue and are being improved in methodology as they progress.

(2) Bedding Plant Growth Stimulation

Potting mix was seeded with *Bradyrhizobium japonicum* at 500,000 and 5,000,000 active cells per ml of mix. Seeds of 8 different bedding plant varieties were sown in the seeded mix and genistein isoflavonoid inducer was applied to the rhizobia in a number of ways from coating the seeds to watering with the signal inducer.

The seeds were then assessed for germination either as increased amount or increased rate. The young seedlings were then assessed for growth as measured by height for a number of weeks while in the seedling trays.

Transplanted Growth

Cherry tomato seedlings (5-week old) were transplanted into 5" pots seeded with rhizobia at 1e6 cells/ml (2 and 20 uM Seed Coater) or without rhizobia (control and LCO treatments). Seed Coater and LCO solutions were prepared with water and 50 ml/plant applied to plant after transplantation. Ripened fruit (orange or red) were collected 8 weeks after transplantation.

BRIEF DESCRIPTON OF THE DRAWINGS

FIG. 1 shows germination rate of seed coater treated soybean seed.

FIG. 2 shows soybean seed germination one month after treatment by seed coater.

FIG. 3 shows effect of seed coater on soybean plant height.

FIG. 4 shows effect of seed coater on corn seed emergence.

Fig, 5 shows effect of seed coater on corn plant height immediately after treatment by seed coater.

FIG. 6 shows effect of seed coater on corn plant height one month after treatment by seed coater.

FIG. 7 shows effect of seed coater transplant formulation on cherry tomato early fruit numbers.

FIG. 8 shows growth promotion of potato tubers with signals grown in the field.

FIG. 9 shows, growth promotion of potato tubers with signals grown in the greenhouse.

Summary: (1) Seed Coater soil applied to transplanted cherry tomato can enhance early fruit number. (2) Seed Coater signals more effective than LCO signal when applied to soil around transplanted roots.

Data List

| Table/Fig number | Crop/parameter | Location | Planted time |
|---|---|---|---|
| FIG. 1 | Soybean/germination | Greenhouse | Immediately |
| FIG. 2 | Soybean/germination | Greenhouse | One month later |
| FIG. 3 | Soybean/height | Greenhouse | Immediately |
| FIG. 4 | Corn/germination | Greenhouse | Immediately |
| FIG. 5 | Corn/height | Greenhouse | Immediately |
| FIG. 6 | Corn/height | Greenhouse | One month later |
| FIG. 7 | Tomato Transplant Fruit Number | | |
| FIG. 8 | Growth Promotion of Potato Tubers With Signals | Field | |
| FIG. 9 | Growth Promotion of Potato Tubers With Signals | Greenhouse | |
| Table 1 | Soybean/nodule | Greenhouse | Immediately |
| Table 2 | Soybean/nodule | Greenhouse | One month later |
| Table 3 | Corn/dry weight | Greenhouse | Immediately |
| Table 4 | Corn/dry weight | Greenhouse | One month later |

-continued

| Table/Fig number | Crop/parameter | Location | Planted time |
|---|---|---|---|
| Table 5 | Corn/yield | Field | Immediately |
| Table 6 | Soybean/germination/yield | Field | 5 weeks |
| Table 7 | Soy/nodule/biomass | Field | 5 weeks |
| Table 8 | Pea/germination/nodule/biomass/yield | Field | Immediately |
| Table 9 | Soybean/yield | 5 field sites | Immediately |
| Table 10 | Wheat/germination | Field | Immediately |
| Table 11 | Corn/germination | 5 field sites | Immediately |
| Table 12 | Soybean/germination/yield | 2 field sites | Immediately |
| Table 13 | SeedCoater timing studies on soybeans and corn grown in greenhouse. Treatment of seed Coater increased plant biomass and soybean nodulation 4-5 weeks after planting. The efficacy kept up to 60 days after treatments. | | |
| Table 14 | SeedCoater treatments at different strengths on soybeans in field trials. The same experiment was conducted in Quebec and Ontario. Treatments of seedCoater from 300-800 uM increased soybean yield; yield from Ontario was statistical. | | |
| Table 15 | Comparison of SeedCoater formulations on soybeans in Quebec and Ontario. A formulation of seedCoater containing two isoflavonoids performed better than one with a single isoflavonoid at the same strength. | | |
| Table 16 | SeedCoater treatment on various soybean varieties in field trials at NK Canada. Five of 6 soybean varieties treated with seedCoater showed yield benefit of 2.2 bu/ac using 300 uM seedCoater. | | |
| Table 17 | SeedCoater plus seed treatments and inoculants on soybean in field trials. SeedCoater with or without inoculants performed better than seed treatments alone in soybean land. | | |
| Table 18 | Treatment of seedCoater on pea, soybeans and wheat grown in bean land. SeedCoater of 400 uM as a universal strength increased pea, soybean and wheat yields in field trials. | | |
| Table 19 | Comparison of SeedCoater formulations on grain and silage yield in corn. A formulation (400 uM) of seedCoater with two isoflavonoids performed better than one isoflavonoid in the formulation at the same strength on grain yield when corn was planted 30 days after treatment. | | |
| Table 20 | Corn seedCoater grown in different soil inoculation levels at University of Guelph. SeedCoater treatment resulted in best corn yield at a soil rhizobia level of $10^3$ cells/g soil. SeedCoater at 400 uM significantly increased corn grain yield over control. | | |
| Table 21 | Effect of seedCoater on corn yield when applied one year before planting. SeedCoater treated seed did not reduce percent emergence after 1 year on seed storage at room temperature and increased corn yield up to 19% over seed treatment control. | | |
| Table 22 | SeedCoater field trials on soybeans at multiple sites. SeedCoater with seed treatment increased soybean biomass and grain yield up to 1-2 bu/ac compared to control. | | |
| Table 23 | SeedCoater field trials on corn at multiple sites. SeedCoater with Cruiser raised corn yield from 2 to 41 bu/ac compared to Maxim XL treatment in average of multiple sites. | | |
| Table 24 | Signal applied to tomato seedling roots transplanted into soil inoculated with soybean rhizobia. Early yield were higher than control in fruit number and weight of all treatments. | | |

TABLE 1

Effect of SeedCoater Dose on soybean nodulation when soybean seed treated and sown immediately, Cumulative weight and Number of nodules from 16 plants at 24 days

| Signal applied (uM) | Total Nodule number on 16 plants | Nodule weight (g) of 16 plants | Nodule # vs control | Nodule weight vs. control |
|---|---|---|---|---|
| 0 | 253 | 0.119 | 0 | 0 |
| 50 | 315 | 0.147 | 24.50% | 23.84% |
| 100 | 260 | 0.135 | 2.70% | 13.65% |
| 200 | 281 | 0.121 | 11.20% | 1.50% |
| 300 | 306 | 0.127 | 20.94% | 6.99% |
| 400 | 313 | 0.125 | 23.70% | 5.64% |

Notes:
Greenhouse study conducted in 4" pots inoculated with Apex at $10^5$ cells/g of greenhouse soil before planting, 8 pots per treatment. 100 gram of soybean seed was treated with 0.3 ml of each solution in a plastic bag. Treated seed was planted into pot immediately.

Conclusions:

1. All strengths of Seed Coater treated seed and planted immediately increased nodule number and weight.
2. 50 uM strength proved the best dose for both nodule number and weight when applied and planted immediately.

TABLE 2

Effect of SeedCoater dose on soybean nodulation when soybean seed treated one month in advance of sowing. Cumulative weight and Number of nodules from 16 plants at 23 days

| Signal applied (uM) | Total Nodule number on 16 plants | Nodule weight (g) of 16 plants | Nodule # vs control | Nodule weight vs. control |
|---|---|---|---|---|
| 0 | 336 | 0.18 | 0 | 0 |
| 50 | 373 | 0.19 | 11.01% | 7.22% |
| 100 | 365 | 0.19 | 8.63% | 3.33% |
| 200 | 369 | 0.20 | 9.82% | 11.67% |
| 300 | 410 | 0.24 | 22.02% | 33.89% |
| 400 | 382 | 0.20 | 13.69% | 13.33% |

Notes:

Greenhouse study conducted in 4" pots inoculated with inoculants at $10^5$ cells/g of greenhouse soil before planting, 8 pots per treatment. 100 gram of soybean seed was treated with 0.3 ml of each solution in a plastic bag. Treated seed was stored at room temperature for 30 days.

Conclusions:
1. All strengths of Seed Coater increased nodule number and nodule weight when applied 30 days in advance
2. 300 uM strength was the best dose for both nodule number and weight when applied 30 days in advance.
3. Application of Seed Coater 30 days in advance required a higher dose (300 uM) than when applied and sown immediately (50 uM—Table 1).

TABLE 3

Effect of Seed Coater dose on corn plant dry weight in greenhouse study (Planted immediately after treatment)

| Treatment | Dry weight (gram)/plant | Increased over control % |
|---|---|---|
| 0.0 uM | 0.8367 | |
| 50 uM | 0.9024 | 7.8% |
| 100 uM | 0.8987 | 7.4% |
| 200 uM | 0.9501 | 13.5% |
| 300 uM | 0.9672 | 15.6% |
| 400 uM | 0.9299 | 11.1% |

Notes:
1. Inoculated *Bradyrhizobium japonicum* at $10^5$ cfu/ml in soil
2. Plant at time zero (Table 3) or 1 month later (Table 4)
3. 2 plants/pot and 8 pots/treatment
4. Greenhouse temperature over 30 C. for a few days in April, which affected plant growth in the greenhouse (Table 4) so that plants got bigger compared to plants in Table 3
5. Plants were harvested for biomass 31 days (Table 3) and 32 days (Table 4) after sowing Conclusions:

No difference in plant height was seen, but plant dry matter increased by all treatments (7-15.6% over control) by 31 days after sowing.

TABLE 4

Effect of SeedCoater dose on Corn plant dry weight in greenhouse study (planted 1 month after treatment)

| Treatment | Dry weight (gram)/plant | Increased over control % |
|---|---|---|
| 0.0 uM | 3.0056 | |
| 50 uM | 3.2844 | 8.5% |
| 100 uM | 3.0650 | 1.8% |
| 200 uM | 3.6975 | 21.1% |
| 300 uM | 3.2456 | 7.3% |
| 400 uM | 3.3781 | 11.3% |

Conclusion:

All Seed Coater treatments increased both plant height and dry weight at 32 days after sowing, but dry weight increased up to 21% at applied strength of 200 uM.

TABLE 5

Effect of SeedCoater dose on corn grain yield

| Treatments | Harvested Wet Grain (kg/2 rows) | Wet Grain Yield (kg/ha) | Grain Yield (kg/2 rows) | Grain Yield (kg/ha) |
|---|---|---|---|---|
| 250 uM | 8.05 b | 5963.0 b | 6.53 b | 4840.1 b |
| 400 uM | 9.63 a | 7133.3 a | 7.71 a | 5713.6 a |
| 600 uM | 8.17 b | 6051.9 b | 6.50 b | 4817.0 b |
| Untreated control | 7.63 b | 5244.4 b | 6.14 b | 4546.4 b |
| Significant at 5% | Yes | Yes | Yes | Yes |

Notes:

1. Treated seeds were stored at room temperature (20° C.) for one month before planting
2. Soil was seeded with inoculants at $10^5$ cells/gram soil before planting
3. Seedling stand was examined 1 month after planting and data (not listed) showed that Seed Coater did not affect seed emergence when applied 1 month after treatment.
4. Corn grain was harvested from the two middle rows of each plot (13.5 $M^2$) at MAC farm (Harvesting date: Oct. 30, 2003, Seeding: May 23, 2003)
5. Grain yield corrected to dry weight by drying approx. 500 gram/plot at 60° C. for days.

Conclusions:
1. All treatments of Seed Coater increased corn grain yield by 6%-25.6% over control
2. 400 uM significantly increased both wet and dry grain yield

TABLE 6

Effect of Seed Coater dose on soybean seed germination and final grain yield

| Treatments | Germination % | Yield (Kg/ha) |
|---|---|---|
| 200 μM one month | 46.00a | 2102.19 a |
| 300 μM one month | 37.75b | 1970.14 b |
| 400 μM one month | 42.00ab | 2040.86 a |
| Untreated Control | 39.25b | 1530.57 c |
| Significance at 5% | Yes | Yes |

TABLE 7

Effect of Seed Coater dose on soybean nodulation and biomass

| | Growing Stages | | | | | |
|---|---|---|---|---|---|---|
| | V3 | | | Blooming | | |
| Treatments | Nodule Number on 5 plants | Nodule Dry Weight (g) from 5 plants | Shoot Dry Weight (g) from 5 plants | Nodule Number on 5 plants | Nodule Dry Weight (g) of 5 plants | Shoot Dry Weight (g) of 5 plants |
| 200 μM one month | 122.8 | 0.2281 | 7.9 | 184 | 0.4994 | 21.70 |
| 300 μM one month | 96.5 | 0.2629 | 7.4 | 186 | 0.4994 | 23.56 |
| 400 μM one month | 121.8 | 0.2689 | 6.77 | 161 | 0.4304 | 19.64 |
| Untreated Control | 104.0 | 0.2012 | 5.21 | 164 | 0.4329 | 15.31 |
| Significance at 5% | No | No | No | No | No | No |

Notes:
1. Experiment was conducted on E. Lods farm of McGill University in 2003.
2. Seeds pre-treated by Seed Coater on Apr. 4, 2003 and stored at room temperature (20° C.), and sown on May 30 (5 weeks).
3. Germination or stand % was examined on July 2, counting seedling in 2-meter long row from two middle rows of each plot.
4. Soil was seeded with *rhizobia* at $10^5$ cells/gram on May 30 just before planting
5. Soybean grain in whole plot was harvested by a combine on Oct. 17, 2003

Conclusions:
There were:
1. Increased seed emergence by strength at 200 and 400 uM dosages, and statistically significant at 200 uM strength.
2. Significantly increased grain yield by all treatments.
3. Increased nodulation and biomass by all treatments, however, not statistically.

TABLE 8

Effect of SeedCoater Dose on pea seed emergence, nodulation and yield under field conditions

| Treatments | Stand % | Nodule Number on 5 plants | Nodule Weight (g) of 5 plants | Average nodule weight (mg) | Dry Weight (g) of 5 Shoots | Bu/acre | Increase in bu/ac |
|---|---|---|---|---|---|---|---|
| Control | 95 | 217.75 | 0.2227 | 1.04b | 8.81 | 26.5b | 0 |
| 50 μM | 93 | 265.75 | 0.2633 | 1.13ab | 10.17 | 29.8a | 3.3 |
| 100 μM | 98 | 287.75 | 0.2991 | 1.24ab | 8.61 | 28.0ab | 1.5 |
| 200 μM | 91.25 | 196.25 | 0.2931 | 1.52a | 10.14 | 29.6a | 3.1 |
| 400 μM | 87.5 | 216.5 | 0.2585 | 1.20ab | 9.01 | 29.4a | 2.9 |
| 600 μM | 93 | 245.75 | 0.2970 | 1.33ab | 9.02 | 28.3ab | 1.8 |
| Significant 5% | NS | NS | NS | Yes | NS | Yes | |

Notes:
1. Experiment was conducted on E. Lods farm of McGill University in 2003.
2. Make stock solution of Naringenin (70 mM) and Hesperetin (30 mM) with DMSO and dilute to the strengths needed for each seed treatment with water.
3. Pea seed (cv. Delta) was treated and planed immediately in plots which was seeded with *Rhizobia* at $10^5$ cells/gram of soil.
4. Seed germination was examined on Jun. 9, 2003 (sown on May 16, 2003).
5. Nodulation examined on Jun. 27, 2003 by sampling 5 plants per plot.
6. Pea was harvested on Aug. 6, 2003 using a combine and grain was dried at 60° C. for 3 days.

Conclusions:
1. There is no difference among treatments on extent of germination of pea.
2. Seeds treated with SeedCoater at 100 μM showed the maximum germination. There was no significant difference when compared to control.
3. SeedCoater increased nodulation and biomass, but not significantly. However, nodule weight was significantly improved at 200 uM.
4. Most treatments significantly increased pea grain yield, some up to 3 bu/ac.

TABLE 9

Response in soybean yield (Bu/ac) at 5 sites

| Locations | Treatments | | |
|---|---|---|---|
| | Untreated control | Warden RTA (W-RTA) | W-RTA + Seed Coater |
| Brookston, IN | 32.97 | 31.50 | 40.03 |
| Tolono, IL | 36.43 | 33.80 | 37.73 |
| Walbash, IN | 43.78 | 44.85 | 45.14 |
| Wolcott, IN | 31.03 | 36.70 | 35.83 |
| Mt. Hope, WI | 32.90 | 34.39 | 38.13 |
| Average yield of 5 sites | 35.42 | 36.25 | 39.37 |
| % vs. control | 0.00 | 2.34 | 11.15 |
| % vs. W-RTA | −2.29 | 0.00 | 8.61 |
| Significant at 5% | B | B | A |

Notes:
1. Seeds were treated at 300 uM and planted immediately in repeat soybean lands at 5 sites.
2. High quality soybean seed commercially treated with Fungicide (Warden RTA) was employed in this trial.

Conclusion:
1. Seed Coater significantly increased soybean grain yield over yields from untreated and Warden RTA seeds.

TABLE 10

Effect of SeedCoater Dose on spring wheat seed emergence (%) in field trial
Percent of treated seed emerged at 4 weeks

| Treatments | Replicates | | | | Average |
|---|---|---|---|---|---|
| | 1 | 2 | 3 | 4 | |
| Control | 56 | 64 | 52 | 36 | 52b |
| 100 uM | 68 | 72 | 60 | 64 | 66ab |
| 200 uM | 60 | 72 | 80 | 64 | 69a |
| 400 uM | 60 | 68 | 68 | 76 | 68a |
| 600 uM | 80 | 60 | 80 | 48 | 67ab |

Notes:
1. 100 treated wheat seeds were planted in each plot of field immediately.
2. Spring wheat seed was coated by chemicals.
3. Emergence was examined at 4 weeks after sowing in field.
4. The field trial was terminated because plots were damaged by animals. No yield data available from this trial.

Conclusion:
Seed Coater significantly improved wheat seed emergence at strength of 200-400 uM.

TABLE 11

Effect of Seed Coater treatment on fungicide (Maxim XL) treated corn seed emergence at 5 sites in USA, 2003

| | (% Field Emergence) | | | | | |
|---|---|---|---|---|---|---|
| Treatments | Indiana | Illinois | Iowa (1) | Iowa (2) | Nebraska | Average |
| MaximXL | 86.88 | 86.07 | 76.79 | 58.21 | 84.29 | 78.448b |
| MaximXL + Seed Coater | 85.63 | 85 | 79.29 | 77.5 | 91.07 | 83.698a |

Notes:
1. 250 uM (liquid) of Seed Coater directly applied to corn seed (Hybrid) at 3 ml/kg seed before sowing.
2. Seeds treated with Seed Coater were sown immediately after treatment at 5 sites.
3. Chemical (fungicide) coated corn seed was used in this trial.
4. The Contracted field trials failed and contractor did not submit any yield data.

Conclusions:
Seed Coater significantly improved corn seed emergence.

TABLE 12

Effect of Seed Coater on soybean stand and grain yield in field trials.

| | Plants/M$^2$ | | Grain yield (kg/ha) | |
|---|---|---|---|---|
| Treatment | Huron Park | Ridgetown | Huron Park | Ridgetown |
| Untreated control | 21.2 ab | 56 | 1926 a | 3177 ab |
| Seed Coater | 22.23 a | 49 | 2026 a | 3227 a |
| Inoculant 2 | 19.8 ab | 53 | 1992 a | 2967 c |
| Inoculant 1 | 13.88 b | 47 | 1842 b | 3056 bc |
| Significant | $LSD_{0.05}$ | NS | $LSD_{0.1}$ | $LSD_{0.1}$ |

Notes:
1. Seed Coater treated seed immediately planted in repeat soybean lands.
2. Soybean seed was treated with Seed Coater of 300 uM at 3 ml/kg seeds.

Conclusions:
1. In general, Seed Coater did not negatively affect soybean seed emergence in the fields.
2. Seed Coater increased soybean grain yield over other inoculant treatments and control. However, significance was only seen over control (at 0.1 alpha). The increase was not significant over other inoculant treatments.

TABLE 13

Early growth promotion by pre-treatment of SeedCoater on soybean and corn seeds in greenhouse

| Crops and treatments | Days pre-treatment before planting | | | | | | | |
|---|---|---|---|---|---|---|---|---|
| | Day 0 | | Day 10 | | Day 30 | | Day 60 | |
| Soybeans | Nodules (mg) | Plant height (cm) | Nodules (mg) | Plant height (cm) | Nodules (mg) | Plant height (cm) | Nodules (mg) | Plant height (cm) |
| 300 uM | 195.9 | 41.1 | 264.4 | 53.5 | 222.7 | 72.0 | 183.6 | 67.0 |
| Control | 188.2 | 39.8 | 248.4 | 51.1 | 201.5 | 69.9 | 171.1 | 62.8 |

TABLE 13-continued

Early growth promotion by pre-treatment of SeedCoater on soybean and corn seeds in greenhouse

| Crops and treatments | Days pre-treatment before planting | | | | | | | |
|---|---|---|---|---|---|---|---|---|
| | Day 0 | | Day 10 | | Day 30 | | Day 60 | |
| Corn | Height (cm) | Biomass (mg) | Height (cm) | Biomass (mg) | Height (cm) | Biomass (mg) | Height (cm) | Biomass (mg) |
| 400 uM | N/A | 7.25 | 108.5 | 10.28 | 127.3 | 12.98 | 139.2 | 12.64 |
| Control | N/A | 6.71 | 105.0 | 9.25 | 124.3 | 12.03 | 133.4 | 12.48 |

Notes:
Chemical seed treatments for soybean (Apron Maxx RTA) and corn (Maxim XL) were used in this study. One kg seed was treated with 3 ml of Signal, SeedCoater solution in a plastic bag and treated seeds were stored at 17° C. Five seeds were planted in a 5" pot in 0, 10, 30 and 60 days after treatment, in greenhouse, 10 pots each treatment. Mixture of Sunshine Mix ® and Turfase (1:1) as plant growth medium was inoculated with soybean inoculant $B.\ japonicum$ at $10^5$ cells/g. Seed emergence and stand were counted 7 days after sowing, and each pot thinned to the best two seedlings per pot. Plants were harvested at approximately 30 days and measurements were taken for plant height, biomass and nodulation (soybeans).

Conclusions:
1. Treatment with Signals increased plant biomass and soybean modulation 4-5 weeks after planting. The efficacy kept up to 60 days after treatment.
2. SeedCoater increased soybean plant biomass, height and nodulation up to 60 days after treatment.
3. SeedCoater increased plant biomass and height of corn up to 60 days after treatment.
4. SeedCoater showed no negative effects corn on and soybean seed emergence or stand compared to untreated control.

TABLE 14

Soybean grain Yield Promotion of Soybeans treated with SeedCoater in field trials

| Treatment | Days pre-treatment | Locations | | Average | Increased % over control |
|---|---|---|---|---|---|
| | | VARS | MAC | | |
| 300 uM | 0 | 57.89 | 38.24 | 48.1 | 21.9 |
| | 30 | 51.70 | 48.34 | 50.0 | 26.9 |
| 400 uM | 0 | 59.89 | 43.15 | 51.5 | 30.7 |
| | 30 | 51.70 | 37.86 | 44.8 | 13.6 |
| 500 uM | 0 | 63.69 | 30.22 | 47.0 | 19.1 |
| | 30 | 62.44 | 40.36 | 51.4 | 30.4 |
| 600 uM | 0 | 67.40 | 41.34 | 54.4 | 37.9 |
| | 30 | 52.56 | 33.03 | 42.8 | 8.5 |
| 800 uM | 30 | 52.25 | 37.85 | 45.1 | 14.3 |
| Control | N/A | 39.58 | 39.28 | 39.4 | 0 |

Notes:
Experiments with the same design were conducted at Macdonald Agricultural College (MAC) of McGill University, Quebec and Vaughn Agricultural Research Service Ltd. (VARS), Cambridge. Ontario. Before planting, the soil was inoculated with soybean inoculant at $10^5$ cells/g mixed into the top 20 cm of soil. Bare soybean seeds were treated using various formulations of SeedCoater 30 days in advance of planting or at planting time.

Conclusion:
The use of SeedCoater in concentrations of 300 to 600 uM increased average soybean grain yield at both locations.

TABLE 15

Comparison of one active ingredient (genistein) with two (genistein and daidzein) in SeedCoater formulations used in soybean yield trials at VARS and MAC

| Strength and Ingredients | Days pre-treatment | Locations | | Average (bu/ac) | Increased % over control |
|---|---|---|---|---|---|
| | | VARS | MAC | | |
| 400 uM (G) | 30 | 62.2 | 34.5 | 48.35 | 3.9 |

TABLE 15-continued

Comparison of one active ingredient (genistein) with two (genistein and daidzein) in SeedCoater formulations used in soybean yield trials at VARS and MAC

| Strength and Ingredients | Days pre-treatment | Locations | | Average (bu/ac) | Increased % over control |
|---|---|---|---|---|---|
| | | VARS | MAC | | |
| 400 uM (G/D) | 30 | 67.1 | 38.0 | 52.58 | 13.0 |
| Control | N/A | 58.7 | 34.4 | 46.54 | 0.0 |

Notes:
Experiments with the same design were conducted at Macdonald Agricultural Collect (MAC) of McGill University, Quebec and Vaughn Agricultural Research Service Ltd. (VARS), Cambridge, Ontario. Before planting, the soil was inoculated with soybean inoculant at $10^5$ cells/g mixed into the top 20 cm of soil. Bare soybean seeds were treated using two formulations of SeedCoater 30 days in advance of planting or at planting time.

Conclusions:
1. Results from the two sites indicated that the formulation of two active ingredients in SeedCoater ("G/D") applied on soybean seed increased yield better than the formulation of one ingredient ("G") at the same strength of 400 uM.
2. SeedCoater 'G' was however effective at increasing yield versus the control.

TABLE 16

Grain yield of SeedCoater treatments on various soybean varieties in field trials at Syngenta Seeds (NK) Canada

| Soybean Varieties | Grain yield (bu/ac) | | Maturity (days after planting) | |
|---|---|---|---|---|
| | Untreated | Treated | Untreated | Treated |
| S00-F8 | 40.6 | 44.8 | 114 | 113 |
| S02-M9 | 45.4 | 48.6 | 115 | 114 |
| S04-Z9 | 48.8 | 51.2 | 117 | 117 |
| S08-C3 (X309R) | 54.7 | 56.1 | 122 | 121 |
| S08-V7 (X408R) | 57.7 | 60.7 | 121 | 122 |

TABLE 16-continued

Grain yield of SeedCoater treatments on various soybean varieties in field trials at Syngenta Seeds (NK) Canada

| Soybean Varieties | Grain yield (bu/ac) | | Maturity (days after planting) | |
|---|---|---|---|---|
| | Untreated | Treated | Untreated | Treated |
| S10-T1 | 52.8 | 51.6 | 122 | 123 |
| Mean Yield | 50 | 52.2 | 118.5 | 118.3 |
| $LSD_{0.05}$ | | 0.6 | | |

Notes:
SeedCoater at 300 uM containing 3% of methanol as organic solvent was used in this experiment. Seed was pre-treated for 30 days before planting.

Conclusions:
1. Five of 6 soybean varieties treated with SeedCoater showed a yield benefit using 300 uM SeedCoater.
2. Treatment of SeedCoater significantly increased soybean yield up to 2.2 bu/ac compared to relevant untreated control.

TABLE 17

SeedCoater treatment of soybeans also treated with commercial seed pre-treatment

| Treatment | Days Pre-Treatment | Seed treated by Warden RTA | Seed treated by Yield Shield |
|---|---|---|---|
| 300 uM | 30 | 67.0 | 67.7 |
| 300 uM + Inoculant | 30 + 0 | 66.7 | 67.9 |
| Control | N/A | 64.0 | 65.3 |

Notes:
1. SeedCoater (300 uM) containing 3% of methanol as a solvent was used in this study.
2. Soybean seeds were pre-treated with a commercial seed treatment by The Tryon Group Inc., USA and then treated a second time with SeedCoater 30 days in advance of planting, and then treated a third time using a commercial soybean inoculant applied at planting time (300 uM + inoculant).
3. Treated seeds were planted into land in Woodstock, Illinois that had a history of soybeans.

Conclusions:
1. SeedCoater applied sequentially with or with chemicals increased soybean grain yield up to 2.5 bu/ac compared to control.
2. Chemical seed treatments did not affect efficacy of SeedCoater on soybean yield.
3. The use of inoculants on treated seeds did not provide any additional yield benefit compared to SeedCoater.

TABLE 18

Effects of SeedCoater on yields when applied to field peas, spring wheat and white beans in Eastern Canada

| | Days pre-treatment | Crops | | | | | |
|---|---|---|---|---|---|---|---|
| | | Field Peas | | Spring wheat | | White Beans | |
| Treatment | | Yield (bu/ac) | % over control | Yield (bu/ac) | % over control | Yield (bu/ac) | % over control |
| 400 uM | 0 | 45.57 | 7.0 | 26.78** | 18.1 | 41.06 | 8.9 |
| | 30 | 50.03** | 17.5 | | | | |
| Control | N/A | 42.60 | 0 | 22.67 | 0 | 37.71 | 0 |

**statistically significant at 5%

Notes:
1. Pea and spring wheat trials were conducted at MAC farm in land inoculated with a pea inoculant at $10^5$ cells/g mixed into the top 20 cm soil. The white bean trail was conducted in bean repeat land at the Huron Research Station of Ridgetown College in Exeter, Ontario. Pea seed was treated with SeedCoater 30 days before planting or at planting time (day 0) whereas the spring wheat and white bean seed was treated on the day of planting.
2. The white bean seed was pre-treated using a chemical seed treatment (Apron Maxx), whereas bare pea seed was employed in this study.
3. Application rate of SeedCoater was 10 g/kg for wheat seed and 3 ml/kg for bean and pea seeds.

Conclusions:
1. SeedCoater at 400 uM increased yields of field peas, white beans and spring wheat up to 4 bu/ac compared to correspondent controls.
2. SeedCoater significantly increased yields of field peas at 5% statistical level when applied 30 days before planting
3. SeedCoater significantly increased yields of spring wheat yield at 5% statistical level.

TABLE 19

Comparison of corn yields (grain and silage) from the use of two SeedCoater formulations in field trials conducted at VARS and MAC

| Strength and Ingredient | Days Pre-treatment | VARS | | | MAC | | |
|---|---|---|---|---|---|---|---|
| | | Grain yield (bu/ac) | Increase over control | Silage yield (ton/ha) | Increased % over control | Grain yield (bu/ac) | Increase % over control |
| 400 uM (G) | 0 | | | | | 154.59** | 19.8 |
| 400 uM (G) | 30 | 145.73 | 1.9 | 16.61 | 11.4 | | |
| 400 uM (G/D) | 30 | 159.04 | 11.2 | 15.94 | 6.9 | | |
| Control | N/A | 142.99 | 0 | 14.91 | 0 | 129.05 | 0 |

**Statistically significant compared to relevant control

Notes:
Corn seed was pre-treated with Maxim XL seed treatment, and then treated with SeedCoater. Treated seeds were planted in soil seeded with a soybean inoculant $10^5$ cells/g mixed into the top 20 cm soil. In a second trial at MAC, bare corn seed was treated with SeedCoater and was planted in a field in which soybeans were grown previously, without the addition of soil inoculation, on day 0.

Conclusions:
1. A formulation (400 uM) of seedCoater with two isoflavonoids performed better than one isoflavonoid in the formulation at the same strength on grain yield when corn was planted 30 days after treatment.

2. SeedCoater increased yield of both grain and silage corn in this study.

3. Corn seed treated with SeedCoater at 400 uM of genistein and planted in soybean land without the addition of soybean inoculant on day 0 can significantly increase corn yield up to 19.8% over control.

4. Both formulations of SeedCoater resulted in increased yields.

TABLE 20

Corn SeedCoater study using different inoculation levels of soil

| Main Factor (soil inoculant levels) | Yield (bu/ac) | Sub-factor (Signal levels) | Yield (bu/ac) |
|---|---|---|---|
| 0 | 68.62 | 0 | 67.51 |
| $10^3$ cells/g | 68.66 | 400 uM | 70.97 |
| $10^4$ cells/g | 69.56 | 500 uM | 70.58 |
| $10^5$ cells/g | 67.99 | 600 uM | 66.60 |
| $LSD_{0.05}$ | 6.59 | | 3.28 |

Notes:

The SeedCoater treated seed was planted using conventional tillage near Rockwood, Ontario on a field that has not grown soybeans before and did not contain populations of *Bradyrhizobium japonicum*. The corn trial was arranged as a split plot design with 4 replications, main factor (soil inoculant levels) and sub-factor (signal levels). Each plot was 15 m long by 3 m wide with 4 rows per plot and 75 cm spacing between rows. Plots were inoculated with *B. japonicum* to rates at $10^3$, $10^4$ and $10^5$ cells/g in the top 20 cm soil. SeedCoater was treated onto bare corn seed (hybrid Direct Seed D46) at Agribiotics Inc. over 30 days before planting.

Conclusions:

1. Seedcoater at 400 uM, was the best treatment and increased corn grain yield over control at 5% statistical level.

2. The treatment of SeedCoater at 400-500 uM could increase corn grain yield up 5% over control when planted in soybean inoculant seeded soil.

3. SeedCoater treatment performed best at $10^3$ cells/g soil inoculated rate.

TABLE 21

Effect of SeedCoater on corn yields when applied one year before planting

| | Planted a few days after treatment* | | Planted 1 year after treatment** | |
|---|---|---|---|---|
| Treatment | Emerge % | Yield (bu/ac) | Emerge % | Yield (bu/ac) |
| Maxim XL | 78.4 | 224.85 | 91.95 | 100 |
| Maxim XL + 250 uM Seedcoater | 83.7 | 239.03 | 93.00 | 119.3 |

Notes:

*the emergence percentage was average of 5 sites (same data in Table 11) and corn yield from Nebraska, USA.

**data of emerge and yield came from 2 Illinois sites.

Notes:

The experiment was conducted in multiple field locations in the USA. Emergence data were obtained from 5 sites and yield data was obtained from the Nebraska site. The experiment using 1-year pre-treated corn seeds was arranged in two locations in Illinois by The Tryon Group Inc. in 2004. Pretreated corn seed using Maxim XL (chemical seed treatment) was employed in this study.

Conclusions:

1. Seedcoater treated seed did not reduce emergence percentage after 1 year of storage at room temperature 2. Seedcoater treated seed resulted in increased corn yield up to 19% over seed treatment control.

TABLE 22

SeedCoater field trials on soybeans in multiple sites in USA

| | Planting times* | | | |
|---|---|---|---|---|
| | Early | | Normal | |
| Treatments | G/plant** | Yield (bu/ac) | G/plant** | Yield (bu/ac) |
| Apron-Maxim | 71.18 | 63.5 | 165.00 | 50 |
| Apron-Maxim-Seedcoater | 73.66 | 64.6 | 163.75 | 52 |
| Apron-Maxim-Cruiser-Seedcoater | 78.24 | 65.6 | 177.25 | 52 |

Notes:

*Early planting from April 24 to May 7, 2004, and normal planting on May 20.

**grams - dried weight per plant

Notes:

The average of biomass data (gram/plant) was observed at soybean blooming stages which were different at each site. The yield data in the table were average of 4 sites (Missouri, Wisconsin, SE Iowa, and Minnesota) for early planting and one site (Iowa) for normal. Chemical pre-treated soybean seed was used in this study.

Conclusion:

Seedcoater with seed treatments increased soybean biomass and grain yield up to 1-2 bu/ac compared to control.

TABLE 23

Seedcoater field trials on corn in multiple sites in USA

| | Planting times* | | | |
|---|---|---|---|---|
| | Early | | Normal | |
| Treatments | Higher rate of Cruiser | Lower rate of Cruiser | Higher rate of Cruiser | Lower rate of Cruiser |
| Maxim XL | 180 | 196 | 128 | 170 |
| Maxim XL + Crusier + SeedCoater | 184 | 205 | 169 | 172 |

Notes:

*Corn seeds were planted in the middle of April as "early" planting time and from April 28 to May 3 as "normal" planting time, and corn yield data in table indicate in bu/ac.

Notes:

The field trials were conducted in Stanton, Hampton, Bloomington, Illinois, Iowa, Geneva Minnesota and Wisconsin for early planting studies and Stanton, two sites in Hampton, and two sites in Bloomington for normal planting studies.

Conclusion:

SeedCoater with Maxim XL+Cruiser raised corn yield from 2 to 41 bu/ac compared to Maxim XL alone treatment, in the average of multiple sites in USA.

TABLE 24

Signal applied to tomato seedling roots transplanted into soil inoculated with soybean *rhizobia*

| Treatments | Early Yield | | | | Total Yield | | | |
|---|---|---|---|---|---|---|---|---|
| | Fruit/plot | % vs ctrl | Kg/plot | % vs ctrl | Fruit/plot | % vs ctrl | Kg/plot | % vs ctrl |
| 100 ml water as Control/plant | 58 | 0 | 10.41 | 0 | 219 | 0 | 25.60 | 0 |
| 100 ml genistein at 1 uM/plant | 67.75 | 16.81 | 12.02 | 15.47 | 241.5 | 10.27 | 27.10 | 5.86 |
| 100 ml genistein at 10 uM/plant | 66.25 | 14.22 | 11.64 | 11.82 | 217.75 | −0.57 | 25.91 | 1.21 |
| 100 ml genistein at 50 uM/plant | 71 | 22.41 | 12.85 | 23.44 | 198.5 | −9.36 | 25.77 | 0.66 |

Notes:
1. Soil was inoculated with soybean rhizobia at $10^6$ cells/g mixed into the top 20 cm soil.
2. Tomato seedlings at 6-7 leaf stage were transplanted in field, 6 plants/plot sized 4.5 M by 1.5 M area and 4 replicates each treatment.
3. Applied 100 ml signal solution of each strength or water to transplanted tomato root system.
4. Signal would induce LCO in situ around root system to promote plant growth.
5. Trials were conducted at MacDonald College, McGill University, Montreal.

Conclusions:
1. All treatments increased fruit weight over control.
2. Early yield of fruit numbers of all treatments were higher and the 50 uM rate was statistically higher than control.
3. Early yield of fruit weight of all treatments were higher and the 50 uM rate was statistically higher than control.
4. A similar study was conducted on cherry tomato in greenhouse (see FIG. 7).

Growth Promotion of Potato Tubers with Signals Grown in the Field

Notes:
1. Microtubers (cv. Bintje, tuber size from 0.5-0.7 g) were soaked in each test solution overnight at 25° C. in the incubator. Treatment rate was 50 ml/treatment, and 50 ml water as control.
2. Seeded soybean inoculant into soil at $10^6$ cells/g in the top 20 cm soil before planting.
3. Treated potato tubers were planted in soil 10-15 cm deep, 10 tubers in 10 $M^2$ plot and supplied 500 ml of water to each tuber in ground after planting.
4. Planted date: Aug. 20, 2004 and harvested date: Oct. 15, 2004.

Conclusions:
1. Treatment of potato microtubers soaked in 300 uM genistein solution overnight increased potato tuber yield up to 17.7% over control. See FIG. 8.
2. The higher concentration of treatments (300-500 uM) resulted in larger tuber size. See FIG. 8.

Growth Promotion of Tubers with Signals and Grown in the Greenhouse

Notes:
1. Potato minitubers (cv. Norland, size from 10-15 g) were immersed in each genistein solution overnight (24 hr) at room temperature and planted in 10" pots containing Sunshine Mix seeded with soybean inoculant at $10^6$ cells/g.
2. Greenhouse temperature was maintained at 20/25° C. dark/light.
3. One tuber was planted in each pot and 8 replicates each treatment were completely randomized on two greenhouse benches.
4. Slow release fertilizer (20-20-20) was applied at 50 g/pot.
5. Plated date: Sep. 1, 2004 Harvested date: Nov. 9, 2004

Conclusions:
1. All treatments statistically increased potato tuber yield, and treatment of 300 uM showed the best growth promotion. See FIG. 9.
2. Treated potato seeds exhibited increased sprout numbers for each tuber, and soaking seed in 300 uM solution was the best treatment to stimulate sprout number. See FIG. 9.

Conclusion

The present invention demonstrates that one or more Isoflavonoid compound Signals which may be with an agriculturally acceptable carrier, applied prior to planting, up to 365 days or more, either directly to a non-legume crop or a legume crop, or applied to the soil that will be planted either to a non-legume crop or a legume crop, have utility for the purpose of increasing yield and/or improving seed germination and/or improving earlier seed emergence and/or improving nodulation and/or increasing crop stand density and/or improving plant vigour and/or improving plant growth, and/or increasing biomass, and/or earlier fruiting, all including in circumstances of seedling and plant transplanting.

Although the invention herein has been described as aforesaid by way of one or more preferred embodiments, the skilled person will understand it can be modified without departing from the spirit and nature of the invention as defined in the appended claims.

The invention claimed is:

1. A method of improving plant growth, comprising:
applying, to a non-leguminous seed, a composition that comprises at least one isoflavonoid and that is devoid of nitrogen-fixing bacteria and nod factors,
wherein, upon planting said seed in a growth medium that comprises one or more nitrogen-fixing bacteria, application of said composition results in improved germination of said seed and/or earlier emergence, increased yield, increased stand density, improved vigor, improved growth, increased biomass and/or earlier fruiting of a plant that germinates from said seed, as compared to an untreated control seed.

2. The method of claim 1, wherein said composition is applied to said seed one month before said seed is planted.

3. The method of claim 1, wherein said composition is applied to said seed 60 days before said seed is planted.

4. The method of claim 1, wherein said composition is applied to said seed 365 days or more before said seed is planted.

5. The method of claim 1, wherein said composition further comprises one or more herbicides, fungicides, insecticides, fertilizers and/or growth promoters.

6. The method of claim 1, wherein said at least one isoflavonoid comprises genistein.

7. The method of claim 1, wherein said at least one isoflavonoid comprises daidzein.

8. The method of claim 1, wherein said at least one isoflavonoid comprises genistein and daidzein.

9. The method of claim 1, wherein said plant is grown under growth-limiting conditions.

10. The method of claim 1, wherein said plant is grown under pH stress conditions.

11. The method of claim 1, wherein said plant is grown under water stress conditions.

12. The method of claim 1, wherein said plant is grown under temperature stress conditions.

13. The method of claim 1, wherein said seed is a corn seed.

14. The method of claim 1, wherein said seed is a tomato seed.

15. The method of claim 1, wherein said seed is a wheat seed.

16. The method of claim 1, wherein said method further comprises applying said one or more nitrogen-fixing bacteria to said growth medium.

17. The method of claim 16, wherein said one or more nitrogen-fixing bacteria are applied to said growth medium in an amount ranging from 500,000 to 5,000,000 cells per gram of growth medium.

18. The method of claim 16, wherein said one or more nitrogen-fixing bacteria are applied to said growth medium in an amount ranging from 10,000 to 1,000,000 cells per gram of growth medium.

19. The method of claim 16, wherein said one or more nitrogen-fixing bacteria are applied to said growth medium in an amount ranging from $10^3$ to $10^5$ cells per gram of growth medium.

20. The method of claim 16, wherein said one or more nitrogen-fixing bacteria are applied to said growth medium at concentration of about 100,000 cells per gram of growth medium.

21. The method of claim 16, wherein said one or more nitrogen-fixing bacteria comprises a strain of *Bradyrhizobium japonicum*.

22. The method of claim 1, wherein, upon planting said seed in a growth medium that comprises one or more nitrogen-fixing bacteria, application of said composition results in improved germination of said seed, as compared to an untreated control seed.

23. The method of claim 1, wherein, upon planting said seed in a growth medium that comprises one or more nitrogen-fixing bacteria, application of said composition results in earlier emergence, increased yield, increased stand density, improved vigor, improved growth, increased biomass and/or earlier fruiting of a plant that germinates from said seed, as compared to a plant that germinates from an untreated control seed.

24. The method of claim 1, wherein, upon planting said seed in a growth medium that comprises one or more nitrogen-fixing bacteria, application of said composition results in increased yield of a plant that germinates from said seed, as compared to a plant that germinates from an untreated control seed.

25. The method of claim 1, wherein, upon planting said seed in a growth medium that comprises one or more nitrogen-fixing bacteria, application of said composition results in improved growth of a plant that germinates from said seed, as compared to a plant that germinates from an untreated control seed.

26. A seed treated according to the method of claim 1, wherein said seed exhibits improved germination when planted in a growth medium that comprises one or more nitrogen-fixing bacteria, as compared to an untreated control seed.

27. A seed treated according to the method of claim 1, wherein a plant that germinates from said seed exhibits earlier emergence, increased yield, increased stand density, improved vigor, improved growth, increased biomass and/or earlier fruiting when planted in a growth medium that comprises one or more nitrogen-fixing bacteria, as compared to a plant that germinates from an untreated control seed.

* * * * *